United States Patent [19]

Walther et al.

[11] Patent Number: 5,508,405
[45] Date of Patent: Apr. 16, 1996

[54] QUINUCLIDINES, THEIR USE A MEDICAMENTS AND PROCESSES FOR THEIR PREPARATION

[75] Inventors: Gerhard Walther, Bingen; Karl H. Weber, Gau-Algesheim; Werner Stransky, Gau-Algesheim; Franz J Kuhn, Gau-Algesheim; Enzio Muller, Ingelheim am Rhein; Helmut Ensinger, Ingelheim am Rhein, all of Germany

[73] Assignee: Boehringer Ingelheim GmbH, Ingelheim am Rhein, Germany

[21] Appl. No.: 491,463

[22] Filed: Jun. 16, 1995

Related U.S. Application Data

[62] Division of Ser. No. 241,517, May 12, 1994, Pat. No. 5,451,587, which is a continuation of Ser. No. 984,764, Dec. 3, 1992, abandoned, which is a continuation of Ser. No. 699,020, May 13, 1991, abandoned, which is a continuation of Ser. No. 435,892, Nov. 13, 1989, abandoned.

[30] Foreign Application Priority Data

Nov. 22, 1988 [JP] Japan .................. 38 39 385.0

[51] Int. Cl.$^6$ .................................. C07D 453/02
[52] U.S. Cl. .......................................... 546/133
[58] Field of Search ............................. 546/133

[56] References Cited

PUBLICATIONS

CA 117:90149s Preparation . . . agents. Walther et al., p. 768, 1992.

Primary Examiner—Joseph K. McKane
Attorney, Agent, or Firm—Robert P. Raymond; Alan R. Stempel; Mary-Ellen M. Devlin

[57] ABSTRACT

The invention relates to new quinuclidines, processes for their preparation and their use as medicaments having cholinomimetic properties.

1 Claim, No Drawings

QUINUCLIDINES, THEIR USE A MEDICAMENTS AND PROCESSES FOR THEIR PREPARATION

This is a division of application Ser. No. 241,517, filed May 12, 1994, now U.S. Pat. No. 5,451,587 which is a continuation of application Ser. No. 984,764, filed Dec. 3, 1992, now abandoned, which is a continuation of application Ser. No. 699,020, filed May 13, 1991, now abandoned, which is a continuation of application Ser. No. 435,892, filed Nov. 13, 1989, now abandoned.

The invention relates to new quinuclidines, processes for their preparation and their use as medicaments.

The new quinuclidines correspond to the general formula

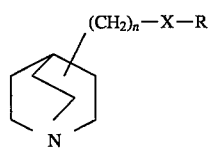

I wherein
R denotes alkyl, alkenyl or alkynyl;
X denotes oxygen or sulphur and
n denotes 0, 1 or 2;

and include all racemates, enantiomers, diastereomers and mixtures thereof, and pharmacologically acceptable acid addition salts thereof and also quaternary salts thereof.

Alkyl groups in the context of this invention are understood as being branched or unbranched alkyl radicals having 1 to 6 carbon atoms, such as e.g. methyl, ethyl, propyl, butyl, pentyl and hexyl, and also branched isomers thereof, such as e.g. iso-propyl, iso-butyl, tert.-butyl etc.; alkenyl groups are understood as being branched or unbranched alkenyl radicals having 3 to 6 carbon atoms—such as e.g. propenyl, butenyl, pentenyl and hexenyl—with a double bond; and alkynyl groups are understood as being branched or unbranched alkinyl radicals having 3 to 6 carbon atoms—such as e.g. propynyl, butynyl and pentynyl—with a triple bond. Those alkenyl or alkinyl radicals in which the double or triple bond is in the terminal position are preferred.

Preferred compounds of the general formula I are those in which X denotes oxygen, n denotes 0 or 1 and the substituent R is in the 3-position and denotes an alkyl group having 1 to 3 carbon atoms, an alkenyl group having 3 or 4 carbon atoms or an alkynyl group having 3 or 4 carbon atoms.

Some compounds of the general formula I are known. Thus, L. Stotter et al. in Heterocycles, Vol. 25 (1987) page 251 et seq. describe the methyl, ethyl and allyl ethers of quinuclidine substituted in the 3-position. The 4-methyl thioether of quinuclidine is known from Helvetica Chim Acta Vol. 57 (1974) page 2339 et seq. The authors do not disclose the use of these substances as medicaments. The 3-methylethyl ether and also the 3-methylethyl thioether are likewise known.

The compounds of the general formula I can be synthesized by a process analogous to the processes described by Stotter. Starting from the N-protected hydroxy- or mercaptoquinuclidines, the compounds according to the invention are obtained by deprotonation with strong bases and subsequent reaction with an alkylating reagent of the general formula Y-R, wherein R is as defined above and Y denotes a leaving group which can easily be split off—such as e.g. halogen, p-toluenesulphonate etc. The reaction is carried out in polar inert organic solvents, such as e.g. dimethylformamide, tetrahydrofuran, dioxane etc. Whereas the deprotonation and conversion of the hydroxy compound into a metal salt is preferably carried out at room temperature or slightly elevated temperature, the subsequent alkylation is preferably carried out while cooling with ice. When the reaction has taken place, the protective group is split off and if appropriate the compounds are converted into their acid addition salts or quaternary compounds, the reaction conditions for this being known and preferred quaternary compounds being the methoiodides and methobromides. Preferred reagents for the deprotonation are sodium hydride, sodium amide and alkali metal alcoholates, such as e.g. potassium tert.-butylate.

The compounds according to the invention have—depending on the position of the side chain—one or two chiral centres. The racemates can be resolved by known methods, such as e.g. by chromatographic resolution processes or by crystallization, if appropriate using chiral or prochiral auxiliaries. Alternatively, the synthesis can be carried out starting from optically active starting compounds.

Wolfgang Eckert et al., Helvetica Chimica Acta, Vol. 57 (1974), 2339 describe a process for the preparation of thioethers of quinuclidines which is primarily suitable for synthesis of derivatives in the 4-position.

The preparation of the hydroxy- or mercaptoquinuclidines of the general formula I—wherein X denotes oxygen or sulphur and R denotes hydrogen, which are suitable as starting compounds, is carried out by analogous processes which are known per se, such as are described, for example, in K. B. Shaw, Canadian Journal of Chemistry, Vol. 43, 3112, (1965) and in DE-OS 19 38 546. The conversion into the corresponding thioethers—starting from the mercaptans—often has already taken place in weakly alkaline solution, c.f.A. Schöbert and A. Wagner in Houben-Weyl, Methoden der organischen Chemie (Methods of Organic Chemistry), Georg Thieme Verlag Stuttgart (1955), page 93 et seq., it being possible to dispense with the protective group required for the oxygen ethers.

The compounds of the general formula I have useful pharmacological properties. Thus, in bonding studies the compounds exhibit affinities for muscarine receptors and muscarine-agonistic GTP shifts (GTP=guanosine triphosphate) (Birdsall, N. I. M., E. C. Hulme and I. M. Stockton 1984 in T.I.P.S. Supplement, Proc. Internat. Symposium on Subtypes of Muscarinic Receptors, Ed. Hirschowitz, Hammer, Giacchetti, Klirns, Levine; Elsevier p. 4–8).

The receptor bonding studies were performed in accordance with the following literature reference [A. Closse, H. Bittiger, D. Langenegger and A. Wahner; Naunyn-Schmiedeberg's Arch. Pharmacol. 335, 372–377 (1987)].

TABLE A

Receptor bonding studies
Radioligand: L(+)cis-[2-methyl-$^3$H]-
N,N,N-trimethyl-1,3-dioxolane-4-methanammonium iodide
NET-647, NEN (New England Nuclear DU PONT).
Organ: Cerebral cortex (rat)

| Example | R | Ki [nmol/l] |
|---|---|---|
| 1 | —CH$_2$—C≡CH | 159 |
| 2 | —CH$_3$ | 8300 |
| 3 | —C$_2$H$_5$ | 410 |
| 4 | -nC$_3$H$_7$ | 220 |

A cholinomimetic action has been demonstrated in vitro and in vivo in pharmacological test models. Thus, for example, 3-(2-propinyloxy)-1-azabicyclo[2,2,2]octane fumarate in a dose of 3 mg/kg i.v. exhibits an arousal reaction typical of cholinomimetics in the EEG (electroencephalogram) of the conscious rabbit.

As muscarine agonists (cholinomimetics), the substances are suitable for therapy of diseases involving impaired function of the cholinergic system.

On the basis of pharmacological findings, the compounds are suitable e.g. for the treatment of the following mentioned diseases: Alzheimer's disease, senile dementia and cognitive disturbances, and the compounds can furthermore be employed for improving memory performance.

Quaternary compounds of the general formula I are particularly suitable for peripheral use, e.g. for glaucoma treatment.

The compounds of the general formula I can be used by themselves or in combination with other active compounds according to the invention, and if appropriate also in combination with other pharmacologically active compounds, e.g. other cerebroactivators. Examples of forms suitable for use are tablets, capsules, suppositories, solutions, elixirs, emulsions or dispersible powders. Corresponding tablets can be obtained, for example, by mixing the active compound or compounds with known auxiliaries, for example inert diluents, such as calcium carbonate, calcium phosphate or lactose, disintegrating agents, such as maize starch or alginic acid, binders, such as starch or gelatin, lubricants, such as magnesium stearate or talc, and/or agents for achieving the depot effect, such as carboxymethylcellulose, cellulose acetate phthalate or polyvinyl acetate. The tablets can also consist of several layers.

Coated tablets can correspondingly be prepared by coating cores prepared analogously to the tablets with the agents customarily used in coated tablet coatings, for example Kollidon or shellac, gum arabic, talc, titanium dioxide or sugar. To achieve a depot effect or to avoid incompatibilities, the core can also consist of several layers. The coated tablet shell can similarly consist of several layers to achieve a depot effect, it being possible for the auxiliaries mentioned above for the tablets to be used.

Elixirs of the active compounds or active compound combinations according to the invention can additionally also contain a sweetener, such as saccharin, cyclamate, glycerol or sugar, and a flavour-improving agent, e.g. flavour substances, such as vanillin or orange extract. They can moreover contain suspending auxiliaries or thickeners, such as sodium carboxymethylcellulose, wetting agents, for example condensation products of fatty alcohols with ethylene oxide, or preservatives, such as p-hydroxybenzoates.

Injection solutions are prepared in the customary manner, e.g. by addition of preservatives, such as p-hydroxybenzoate, or stabilizers, such as alkali metal salts of ethylenediaminetetraacetic acid, and bottled in injection bottles or ampoules.

The capsules containing one or more active compounds or active compound combinations can be prepared, for example, by mixing the active compounds with inert excipients, such as lactose or sorbitol, and encapsulating the mixture in gelatin capsules.

Suitable suppositories can be prepared, for example, by mixing with suitable excipients, such as neutral fats or polyethylene glycol or derivatives thereof.

The therapeutically active individual dose is in the range between 1 and 100 mg.

The following examples illustrate the present invention, but without limiting it in its scope:

Pharmaceutical formulation examples

| A) Tablets | |
|---|---|
| | per tablet |
| Active compound | 80 mg |
| Lactose | 140 mg |
| Maize starch | 240 mg |
| Polyvinylpyrrolidone | 15 mg |
| Magnesium stearate | 5 mg |
| | 480 mg |

The finely ground active compound, lactose and some of the maize starch are mixed with one another. The mixture is sieved, after which it is moistened with a solution of polyvinylpyrrolidone in water, kneaded, subjected to moist granulation and dried. The granules, the remainder of the maize starch and the magnesium stearate are sieved and mixed with one another. The mixture is pressed in to tablets of suitable shape and size.

| B) Tablets | |
|---|---|
| | per tablet |
| Active compound | 60 mg |
| Maize starch | 190 mg |
| Lactose | 55 mg |
| Microcrystalline cellulose | 35 mg |
| Polyvinylpyrrolidone | 15 mg |
| Sodium carboxymethyl-starch | 23 mg |
| Magnesium stearate | 2 mg |
| | 380 mg |

The finely ground active compound, some of the maize starch, the lactose, microcrystalline cellulose and polyvinylpyrrolidone are mixed with one another and the mixture is sieved and processed with the remainder of the maize starch and water in to granules, which are dried and sieved. The sodium carboxymethyl-starch and the magnesium stearate are added, the components are mixed and the mixture is pressed in to tablets of suitable size.

| C) Ampoules | |
|---|---|
| Active compound | 20 mg |
| Sodium chloride | 10 mg |
| Doubly distilled water q.s. ad | 1.0 ml |

PREPARATION

The active compound and the sodium chloride are dissolved in doubly distilled water and the solution is bottled in ampoules under sterile conditions.

| D) Drops | |
|---|---|
| Active compound | 5.0 g |
| Methyl p-hydroxybenzoate | 0.1 g |
| Propyl p-hydroxybenzoate | 0.1 g |
| Demineralized water q.s. ad | 100.0 ml |

PREPARATION

The active compound and the preservatives are dissolved in demineralized water and the solution is filtered and bottled in bottles of 100 ml each.

EXAMPLE 1

3-(2-Propynyloxy)-1-azabicyclo[2,2,2]octane

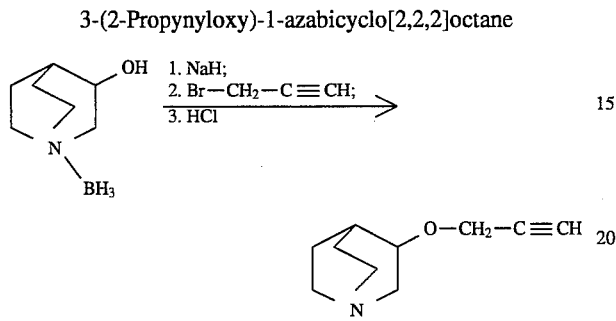

14.1 g (0.1 tool) 3-hydroxy-1-azabicyclo[2,2,2]octane-borane complex are converted into the sodium salt with 4 g sodium hydride dispersion (60% in oil) in 140 ml dimethylformamide at room temperature under nitrogen. When the evolution of hydrogen has ended, a solution of 14.28 g (0.12 mol) propargyl bromide in 10 ml toluene is added to the reaction mixture, while cooling with ice, and the mixture is stirred at room temperature for three hours and, after addition of 5 ml ethanol, concentrated in vacuo on a rotary evaporator. The residue is added to a mixture of 10% sodium chloride solution and ether. The organic phase is dried over anhydrous sodium sulphate and evaporated, The dark brown oil which remains is taken up in 75 ml tetrahydrofuran and 15 ml acetone. 30 ml 4 N hydrochloric acid are added dropwise to the solution formed, while cooling with ice (evolution of gas). The mixture is allowed to after-react at room temperature for a further hour and the organic solvent is distitled off. The residue is diluted with a little water and the mixture is extracted by shaking successively with petroleum ether (40°–60°) and ether. The aqueous phase is rendered alkaline with 40% potassium carbonate solution and extracted with ether. The ether solution is dried over anhydrous sodium sulphate and concentrated. 6.9 g (41.8% of theory) 3-(2-propynyloxy)-1-azabicyclo[ 2,2,2]octane base are obtained and are converted into the fumarate (m.p. 138°–140° C.; from ethanol/ether) with one equivalent of fumaric acid.

| | $C_{10}H_{15}NO \times C_4H_4O_4$ (281.31) | | |
|---|---|---|---|
| calc. | C 59.77 | H 6.81 | N 4.98 |
| found | 59.86 | 6.76 | 4.95 |

$^1$H NMR (CH$_3$OD): σ 6.66 (s, 2H, FU CH); 4.25 (d, 2H, J=3 Hz, OCH$_2$); 4.11 (m, 1H, OCH); 3.67-3.12 (m, 6H, 3 NCH$_2$); 2.93 (t, 1H, J=3 Hz, ≡CH); 2.46-1.70 (m, 5H, —CH$_2$—CH—CH$_2$—).

The following are prepared analogously:

EXAMPLE 2

3-(n-Propyloxy)-1-azabicyclo[2,2,2]octane m.p. 120°–121° C. (CH$_3$CN), fumarate According to microanalysis and the NMR spectrum, the substance contains 1.5 mol fumaric acid.

| | $C_{10}H_{19}NO \times 1.5\ C_4H_4O_4$ (343.38) | | |
|---|---|---|---|
| calc. | C 55.97 | H 7.34 | N 4.08 |
| found | 55.67 | 7.51 | 4.09 |

EXAMPLE 3

3-Methoxy-1-azabicyclo[2,2,2]octane m.p. 72°–74° C. (ethyl acetate/ether), maleate According to microanalysis and the NMR spectrum, the substance contains 1.5 mol maleic acid.

| | $C_8H_{15}NO \times 1.5\ C_4H_4O_4$ (315.33) | | |
|---|---|---|---|
| calc. | C 53.66 | H 6.73 | N 4.83 |
| found | 53.33 | 6.71 | 4.44 |

EXAMPLE 4

3-Ethoxy-1-azabicyclo[2,2,2]octane m.p. 96°–98° C. (acetone/ether), maleate

| | $C_9H_{17}NO \times C_4H_4O_4$ (271.33) | | |
|---|---|---|---|
| calc. | C 57.55 | H 7.80 | N 5.16 |
| found | 57.40 | 8.01 | 5.18 |

$^1$H NMR (CD$_3$OD): σ 6.23 (s, 2H, MA=CH); 3.55 (qu, 2H, J=7 Hz, OCH$_2$):3.98-3.08 (m, 7H, 3 N-CH$_2$, 1 CHO); 2.43-1.68 (m, 5H, —CH$_2$—CH—CH$_2$).

EXAMPLE 5

3-Allyloxy-1-azabicyclo[2,2,2]octane m.p. 129°–132° C. (methanol/ether), fumarate

| | $C_{10}H_{17}NO \times C_4H_4O_4$ (283.33) | | |
|---|---|---|---|
| calc. | C 59.35 | H 7.47 | N 4.94 |
| found | 59.19 | 7.64 | 5.03 |

$^1$H NMR (CD$_3$OD): σ 6.66 (S, 2H, FU=CH): 5.90 (m, 1H,=CH); 5.21 (m, 2H,=CH$_2$); 4.03 (m, 2H, OCH$_2$); 4.14-3.09 (m, 7H, 3 N-CH$_2$); 2.45-1.69 (m, 5H, —CH$_2$—CH-CH$_2$—).

EXAMPLE 6

Racemate splitting of
3-(2-propynyloxy)-1-azabicyclo[2,2,2]octane a.) (+)-3-(2-Propynyloxy)-1-azabicyclo[2,2,2]octane fumarate 16 g (96.82 mmol) 3-(2-propynyloxy)-1-azabicyclo[2,2,2]octane base and 18.22 g (48.41 mmol) (−)-dibenzoyl-L-tartaric acid monohydrate are dissolved in 160 ml acetonitrile, while heating. Multiple crystallization gives the corresponding dibenzoyl tartrate of m.p. 149°–150° C. (decomp.)
$[\alpha]_D$ −43.1° (c=1; $H_2O$)

The salt thus obtained is dissolved in a little water and the solution is rendered alkaline with aqueous 40% potassium carbonate solution and extracted twice by shaking with ethyl acetate. The combined organic phases are dried over anhydrous sodium sulphate and concentrated. 0.8 g (4.9 mmol) of the resulting colourless oil and 0.56 g (4.9 mmol) fumaric acid are dissolved in a little ethanol. Addition of ether gives the title compound of m.p. 145°–147° C.
$[\alpha]_D$ +35.2° (c=1; $H_2O$)

|       | C     | H     | N     |
|-------|-------|-------|-------|
| calc.: | 59.77 C | 6.81 H | 4.98 N |
| found: | 59.75 C | 6.99 H | 5.15 N | b) (−)-3-(2-Propynyloxy)-1-azabicyclo[2,2,2]octane fumarate

The mother liquor described under a) is concentrated and the residue is converted into the base. 8 g (0.048 mol) base and 9.11 g (0.024 mol) (+)-dibenzoyl-D-tartaric acid monohydrate are dissolved in acetonitrile. A procedure analogous to a) gives the benzoyl tartrate (m.p.: 145°–150° C. (decomp), $[\alpha]_D$+43.4° (c=1; $H_2O$)) and from this 2.1 g title compound of m.p. 145°–147° C.
$[\alpha]_D$ −35° (c=1; $H_2O$)

|       | C     | H     | N     |
|-------|-------|-------|-------|
| calc.: | 59.77 C | 6.81 H | 4.98 N |
| found: | 59.79 C | 7.05 H | 4.97 N |

EXAMPLE 7

3-(2-Butynyloxy)-1-azabicyclo[2,2,2]octane m.p. 131°–132° C. (acetonitrile), fumarate

| $C_{11}H_{17}NO \times C_4H_4O_4$ (295.34) | | | |
|---|---|---|---|
| calc. | C 61.00 | H 7.17 | N 4.74 |
| found | 60.92 | 7.40 | 4.70 |

EXAMPLE 8

3-(2-Methyl-propyloxy)-1-azabicyclo[2,2,2]octane m.p. 120°–122° C. (methanol/ether), fumarate According to microanalysis and the NMR spectrum, the substance contains 1.5 tool fumaric acid

| $C_{11}H_{21}NO \times 1.5\ C_4H_4O_4$ (357.41) | | | |
|---|---|---|---|
| calc. | C 57.13 | H 7.61 | N 3.92 |
| found | 57.48 | 7.66 | 4.10 |

EXAMPLE 9

3-Methoxymethyl-1-azabicyclo[2,2,2]octane m.p. 133°–136° C. (ethanol/ether), fumarate

| $C_9H_{17}NO \times C_4H_4O_4$ (271.32) | | | |
|---|---|---|---|
| calc. | C 57.55 | H 7.80 | N 5.15 |
| found | 57.20 | 7.87 | 5.12 |

EXAMPLE 10

3-Ethoxymethyl-1-azabicyclo[2,2,2]octane m.p. 73°–77° C. (ethanol/ether), fumarate

| $C_{10}H_{19}NO \times C_4H_4O_4 \times H_2O$ (303.36) | | | |
|---|---|---|---|
| calc. | C 55.43 | H 8.31 | N 4.62 |
| found | 55.15 | 8.19 | 4.52 |

EXAMPLE 11

3-(2-Propynyloxymethyl)-1-azabicyclo[2,2,2]octane m.p. 88°–90° C. (acetonitrile), oxalate
The substance crystallizes with 1.5 mol oxalic acid.

| $C_{11}H_{17}NO \times 1.5\ C_2H_2O_4$ (314.32) | | | |
|---|---|---|---|
| calc. | C 53.50 | H 6.41 | N 4.46 |
| found | 53.67 | 6.66 | 4.59 |

EXAMPLE 12

3-Allylmercapto-1-azabicyclo[2,2,2]octane 2.86 g (0.02 mol) 3-mercapto-1-azabicyclo[2,2,2]octane are dissolved in 30 ml dimethylformamide and converted into the potassium salt by addition of 2.24 g (0.02 mol) potassium tert.-butylate under nitrogen. 2.42 g (0.02 mol) allyl bromide are then added, while stirring and cooling with ice. The reaction mixture is stirred at room temperature for 45 minutes, acidified with dilute hydrochloric acid and concentrated in vacuo. The residue is dissolved in a little water and the solution is rendered alkaline with 40% potassium carbonate solution and extracted with ether. The organic phase is dried and evaporated. A methanolic solution of the residue is filtered over a silica gel column. Evaporation of the solvent gives 2.9 g crude base, which are converted into the oxalate.

m.p. 90°–92° C. (acetonitrile/ether)

| | C$_{10}$H$_{17}$NS × 1.5 C$_2$H$_2$O$_4$ (318.38) | | | |
|---|---|---|---|---|
| calc. | C 49.04 | H 6.33 | N 4.10 | S 10.07 |
| found | 48.89 | 6.42 | 4.44 | 10.21 |

EXAMPLE 13

3-Ethylmercapto-1-azabicyclo[2,2,2]octane m.p. 101°–102° C. (acetonitrile/ether), oxalate

| | C$_9$H$_{17}$NS × 1.5 C$_2$H$_2$O$_4$ (306.37) | | | |
|---|---|---|---|---|
| calc. | C 47.05 | H 6.58 | N 4.57 | S 10.47 |
| found | 47.16 | 6.92 | 4.70 | 10.63 |

EXAMPLE 14

(−)-3-(Propynyloxy)-1-azabicyclo[2,2,2]octane 100 ml of a 1-molar solution of borane-tetrahydrofuran complex in tetrahydrofuran are added to a suspension of 12.72 g (0.1 mol) (R)-3-quinuclinidol [Lit. B. Ringdahl et al., Acta Pharma Sueg. 16. 281 et seq. (1979)] in 200 ml absolute tetrahydrofuran at 0° C. under nitrogen and while stirring. The reaction solution is subsequently stirred at room temperature for an hour and then evaporated in vacuo. The oily residue is added to a mixture of, methylene chloride and saturated sodium chloride solution. The organic phase is dried over anhydrous sodium sulphate and concentrated. The resin which remains is crystallized with cyclohexane. 12 g (85.1% of theory) (R)-3-quinuclidinol-borane complex are obtained;

m.p. 186°–189° C. (decomp.)

Reaction with propargyl bromide analogously to example 1 gives (−)-3-(2 -propynyloxy)-1-azabicyclo[2,2,2]octane. The crude base is purified by distillation [b.p. 121°/20mb] and converted into the acid fumarate. For this, the base is dissolved in methanol with one equivalent of fumaric acid and the salt is precipitated by addition of ether.

mp. 149°–151° C.; [∝]$_D^{23}$−36.3° (c=1; H$_2$O)

EXAMPLE 15

(+)-3-(Propynyloxy)-1-azabicyclo[2,2,2]octane

Starting from (S)-3-quinuclinidol, the title compound is obtained as the hydrogen fumarate analogously to example 14.

m.p. 149°–151° C.; [∝]$_d^{23}$+36.5° (c=1; H$_2$O)

EXAMPLE 16

(−)-3-Ethoxy-1-azabicyclo[2,2,2]octane is obtained analogously to example 14 from (R)-3-quinuclinidol and ethyl iodide. b.p. 88°–90° C./20 mb; hydrogen fumarate:

m.p. 148°–149° C.; [∝]$_D^{23}$−27.2° (c=1; H$_2$O)

| | C$_9$H$_{17}$NO × C$_4$H$_4$O$_4$ (271.32) | | |
|---|---|---|---|
| calc. | C 57.55 | H 7.80 | N 5.16 |
| found | 57.61 | 7.96 | 5.29 |

The (+)-rotatory enantiomer is obtained correspondingly from (S)-3 -quinuclinidol.

m.p. 148°–149° C.; [∝]$_D^{23}$+27.4° (c=1; H$_2$O)

We claim:

1. 3-(2-propynyloxymethyl)-1-azabicyclo[2,2,2] octane, or a pharmaceutically acceptable acid addition salt thereof.

* * * * *